(12) United States Patent
Burwinkel et al.

(10) Patent No.: US 11,559,252 B2
(45) Date of Patent: Jan. 24, 2023

(54) HEARING ASSISTANCE DEVICE INCORPORATING VIRTUAL AUDIO INTERFACE FOR THERAPY GUIDANCE

(71) Applicant: Starkey Laboratories, Inc., Eden Prairie, MN (US)

(72) Inventors: Justin R. Burwinkel, Eden Prairie, MN (US); Carlos Renato Nakagawa, Eden Prairie, MN (US); Jason Galster, Minneapolis, MN (US)

(73) Assignee: Starkey Laboratories, Inc., Eden Prairie, MN (US)

(*) Notice: Subject to any disclaimer, the term of this patent is extended or adjusted under 35 U.S.C. 154(b) by 127 days.

(21) Appl. No.: 15/589,298

(22) Filed: May 8, 2017

(65) Prior Publication Data
US 2018/0317837 A1    Nov. 8, 2018

(51) Int. Cl.
*G09B 21/00* (2006.01)
*A61B 5/00* (2006.01)
(Continued)

(52) U.S. Cl.
CPC ............ *A61B 5/486* (2013.01); *A61B 3/113* (2013.01); *A61B 5/1114* (2013.01); *A61B 5/741* (2013.01); *A61B 5/742* (2013.01); *A61B 5/7455* (2013.01); *G06F 3/012* (2013.01); *G06F 3/013* (2013.01); *G06F 3/167* (2013.01); *G09B 21/006* (2013.01); *H04R 5/033* (2013.01); *H04R 25/554* (2013.01); *H04S 7/304* (2013.01); *A61B 2505/09* (2013.01);
(Continued)

(58) Field of Classification Search
CPC ...................................... A61B 5/486

USPC ......................................... 434/116
See application file for complete search history.

(56) References Cited

U.S. PATENT DOCUMENTS 4,522,072 A    6/1985   Sulouff et al.
5,916,181 A *  6/1999   Socci et al. ............. A61B 5/00
                                                     600/595
(Continued)

FOREIGN PATENT DOCUMENTS

EP    2700907    2/2014
EP    2725818    4/2014
(Continued)

OTHER PUBLICATIONS

EP Search Report dated Oct. 8, 2018 from EP App. No. 18171323.1, 10 pages.
(Continued)

*Primary Examiner* — Kesha Frisby
(74) *Attorney, Agent, or Firm* — Pauly, DeVries Smith & Deffner LLC

(57) ABSTRACT

A hearing assistance device adapted to be worn by a wearer comprises a processor configured to generate a sequence of audio cues that audibly guide the wearer through a series of actions involving the wearer's head and neck in accordance with a predetermined corrective or therapeutic maneuver. A speaker is configured to play back the sequence of audio cues for reception by the wearer. One or more sensors are configured to sense movement of the head during each of the actions. The processor is configured to determine if head movement for an action associated with each audio cue has been correctly executed by the wearer, and produce an output indicative of successful or unsuccessful execution of the actions by the wearer.

21 Claims, 9 Drawing Sheets

(51) Int. Cl.
*G06F 3/01* (2006.01)
*G06F 3/16* (2006.01)
*H04R 5/033* (2006.01)
*H04S 7/00* (2006.01)
*A61B 5/11* (2006.01)
*A61B 3/113* (2006.01)
*H04R 25/00* (2006.01)
*A63B 71/06* (2006.01)

(52) U.S. Cl.
CPC .......... *A61B 2562/0219* (2013.01); *A61B 2562/0223* (2013.01); *A63B 2071/063* (2013.01); *A63B 2071/0625* (2013.01); *H04S 2400/11* (2013.01)

(56) References Cited

U.S. PATENT DOCUMENTS

| | | | |
|---|---|---|---|
| 6,568,396 B1 * | 5/2003 | Anthony | A61B 5/11 128/897 |
| 6,609,523 B1 | 8/2003 | Anthony | |
| 6,758,218 B2 | 7/2004 | Anthony | |
| 7,490,611 B2 * | 2/2009 | Bromwich | A61B 5/1126 128/897 |
| 7,602,301 B1 | 10/2009 | Stirling et al. | |
| 7,892,180 B2 | 2/2011 | Epley | |
| 8,092,398 B2 | 1/2012 | Weinberg et al. | |
| 8,162,846 B2 | 4/2012 | Epley | |
| 8,308,665 B2 | 11/2012 | Harry et al. | |
| 8,452,273 B1 | 5/2013 | Khomenko et al. | |
| 8,494,507 B1 | 7/2013 | Tedesco et al. | |
| 8,559,914 B2 | 10/2013 | Jones | |
| 8,585,589 B1 | 11/2013 | Cinberg | |
| 8,652,040 B2 | 2/2014 | Leboeuf et al. | |
| 8,737,951 B2 | 5/2014 | Jones et al. | |
| 9,049,558 B2 | 6/2015 | Jones et al. | |
| 9,149,222 B1 | 10/2015 | Zets et al. | |
| 9,167,356 B2 | 10/2015 | Higgins et al. | |
| 9,179,862 B2 | 11/2015 | Stergiou et al. | |
| 9,216,132 B2 | 12/2015 | Aoki et al. | |
| 9,226,706 B2 | 1/2016 | Uehara et al. | |
| 9,414,784 B1 | 8/2016 | Berme et al. | |
| 9,452,101 B2 | 9/2016 | Tomlinson et al. | |
| 9,877,668 B1 | 1/2018 | Sarkar et al. | |
| 9,918,663 B2 | 3/2018 | Singhatat | |
| 9,936,916 B2 | 4/2018 | Sahin | |
| 10,015,579 B2 | 7/2018 | Boesen | |
| 10,149,798 B2 | 12/2018 | Roth | |
| 10,178,970 B2 | 1/2019 | Oddsson et al. | |
| 10,242,590 B2 | 3/2019 | Yu | |
| 10,271,790 B2 | 4/2019 | Lee | |
| 2002/0170193 A1 | 11/2002 | Townsend et al. | |
| 2004/0234933 A1 * | 11/2004 | Dawson | G09B 23/28 434/262 |
| 2005/0046576 A1 | 3/2005 | Julian | |
| 2006/0251334 A1 | 11/2006 | Oba et al. | |
| 2007/0015611 A1 | 1/2007 | Noble et al. | |
| 2007/0177103 A1 | 8/2007 | Migliaccio et al. | |
| 2007/0200927 A1 | 8/2007 | Krenik | |
| 2008/0249736 A1 | 10/2008 | Prstojevich | |
| 2009/0058660 A1 | 3/2009 | Torch | |
| 2009/0240172 A1 | 9/2009 | Fernandez et al. | |
| 2010/0075806 A1 * | 3/2010 | Montgomery | A63B 24/0006 482/8 |
| 2012/0092156 A1 | 4/2012 | Tran | |
| 2012/0219180 A1 | 8/2012 | Mehra | |
| 2014/0002586 A1 | 1/2014 | Nourbakhsh | |
| 2015/0018724 A1 | 1/2015 | Hsu et al. | |
| 2015/0209212 A1 | 7/2015 | Duguid | |
| 2016/0033280 A1 | 2/2016 | Moore | |
| 2016/0070122 A1 | 3/2016 | Sales et al. | |
| 2016/0262608 A1 | 9/2016 | Krueger | |
| 2016/0263437 A1 | 9/2016 | Kow et al. | |
| 2016/0275805 A1 | 9/2016 | Reichow | |
| 2017/0156965 A1 | 6/2017 | Geisinger et al. | |
| 2017/0188895 A1 | 7/2017 | Nathan | |
| 2017/0197115 A1 | 7/2017 | Cook et al. | |
| 2017/0229041 A1 | 8/2017 | Reichow et al. | |
| 2017/0273616 A1 | 9/2017 | Yang et al. | |
| 2017/0274219 A1 | 9/2017 | Ernst et al. | |
| 2017/0291065 A1 | 10/2017 | Klopman | |
| 2017/0360364 A1 | 12/2017 | Heasman et al. | |
| 2018/0092572 A1 | 4/2018 | Sanchez et al. | |
| 2018/0093121 A1 | 4/2018 | Matsuura et al. | |
| 2018/0228404 A1 | 8/2018 | Bhunia et al. | |
| 2018/0234781 A1 | 8/2018 | Stewart et al. | |
| 2018/0250494 A1 | 9/2018 | Hanbury | |
| 2018/0279915 A1 | 10/2018 | Huang et al. | |
| 2018/0279919 A1 | 10/2018 | Bansbach et al. | |
| 2018/0289287 A1 | 10/2018 | Sio et al. | |
| 2019/0117121 A1 | 4/2019 | Kutina et al. | |
| 2019/0246890 A1 | 8/2019 | Kerasidis et al. | |
| 2020/0138364 A1 | 5/2020 | Fabry et al. | |
| 2020/0143703 A1 | 5/2020 | Fabry et al. | |

FOREIGN PATENT DOCUMENTS

| | | |
|---|---|---|
| EP | 3075306 | 10/2016 |
| EP | 3131027 | 2/2017 |
| EP | 1983896 | 6/2017 |
| EP | 3402218 | 11/2018 |
| EP | 3591990 | 1/2020 |
| WO | 2015164456 | 10/2015 |
| WO | 2016097746 | 6/2016 |
| WO | 2017023864 | 2/2017 |
| WO | 2018127851 | 7/2018 |
| WO | 2018223505 | 12/2018 |
| WO | 2019073473 | 4/2019 |
| WO | 2019086997 | 5/2019 |

OTHER PUBLICATIONS

"International Search Report and Written Opinion," for PCT Application No. PCT/US2019/060298 dated Apr. 28, 2020 (20 pages).
Choi, W. J. et al., "Effect of Neck Flexor Muscle Activation on Impact Velocity of the Head During Backward Falls in Young Adults," Clinical Biomechanics 49 (2017), pp. 28-33.
Coburn, Courtney et al., "The Comfort Bud: Designed with Patients in Mind," Starkey Hearing Technologies Product Sheet, 2017 (2 pages).
Farrell, Lisa et al., "Vestibular Rehabilitation: An Effective, Evidence-Based Treatment," Vestibular Disorders Association 2015 (11 pages).
"International Search Report and Written Opinion," for PCT Application No. PCT/US2019/060296 dated Apr. 14, 2020 (15 pages).
Salisbury, Joseph P. et al., "Patient Engagement Platform for Remote Monitoring of Vestibular Rehabilitation with Applications in Concussion Management and Elderly Fall Prevention," 2018 IEEE International Conference on Healthcare Informatics, pp. 422-423.
"International Preliminary Report on Patentability," for PCT Application No. PCT/US2019/060296 dated May 20, 2021 (9 pages).
"International Preliminary Report on Patentability," for PCT Application No. PCT/US2019/060298 dated May 20, 2021 (14 pages).
"Non-Final Office Action," for U.S. Appl. No. 16/677,231 dated Jun. 8, 2021 (35 pages).
"Final Office Action," for U.S. Appl. No. 16/677,231 dated Nov. 16, 2021 (19 pages).
"Response to Non-Final Office Action," for U.S. Appl. No. 16/677,231, filed Sep. 8, 2021 (15 pages).

* cited by examiner

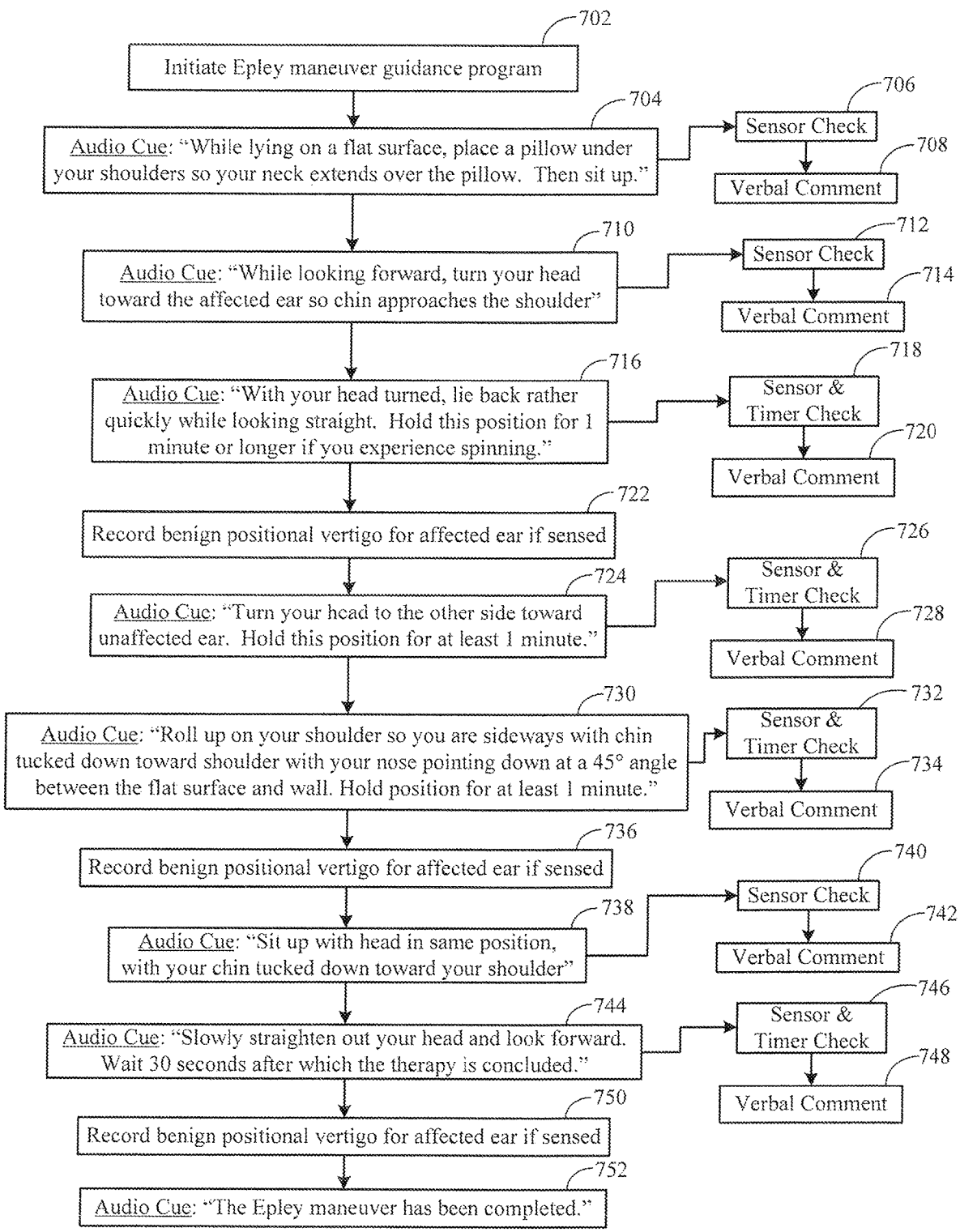

HEARING ASSISTANCE DEVICE INCORPORATING VIRTUAL AUDIO INTERFACE FOR THERAPY GUIDANCE

TECHNICAL FIELD

This application relates generally to hearing assistance devices, including hearing aids, personal amplification devices, and other hearables.

BACKGROUND

Therapeutic maneuvers, therapeutic exercises, and personal training and fitness routines can be very difficult for individuals to learn or perform alone. These activities generally require in-person instruction provided by a healthcare or fitness professional. Often, repeated in-person training sessions are required to ensure that the subject individual properly and safely performs the required maneuvers or exercises.

SUMMARY

Various embodiments are directed to a method implemented by a hearing assistance device adapted to be worn by a wearer. The method comprises generating, by the hearing assistance device, a sequence of audio cues that audibly guide the wearer through a series of actions involving the wearer's head and neck in accordance with a predetermined corrective or therapeutic maneuver. The method comprises sensing, using one or more sensors of the hearing assistance device, movement of the head during each of the actions. The method also comprises determining, by a processor of the hearing assistance device, if head movement for an action associated with each audio cue has been correctly executed by the wearer. The method further comprises producing, by the processor, an output indicative of successful or unsuccessful execution of the actions by the wearer.

According to other embodiments, a hearing assistance device adapted to be worn by a wearer comprises a processor configured to generate a sequence of audio cues that audibly guide the wearer through a series of actions involving the wearer's head and neck in accordance with a predetermined corrective or therapeutic maneuver. A speaker is configured to play back the sequence of audio cues for reception by the wearer. One or more sensors are configured to sense movement of the head during each of the actions. The processor is configured to determine if head movement for an action associated with each audio cue has been correctly executed by the wearer, and produce an output indicative of successful or unsuccessful execution of the actions by the wearer.

The above summary is not intended to describe each disclosed embodiment or every implementation of the present disclosure. The figures and the detailed description below more particularly exemplify illustrative embodiments.

BRIEF DESCRIPTION OF THE DRAWINGS

Throughout the specification reference is made to the appended drawings wherein:

FIG. 7 is a flow chart showing various processes performed by a hearing assistance device that includes a virtual audio interface in accordance with various embodiments;

The figures are not necessarily to scale. Like numbers used in the figures refer to like components. However, it will be understood that the use of a number to refer to a component in a given figure is not intended to limit the component in another figure labeled with the same number;

DETAILED DESCRIPTION

Figure 1:
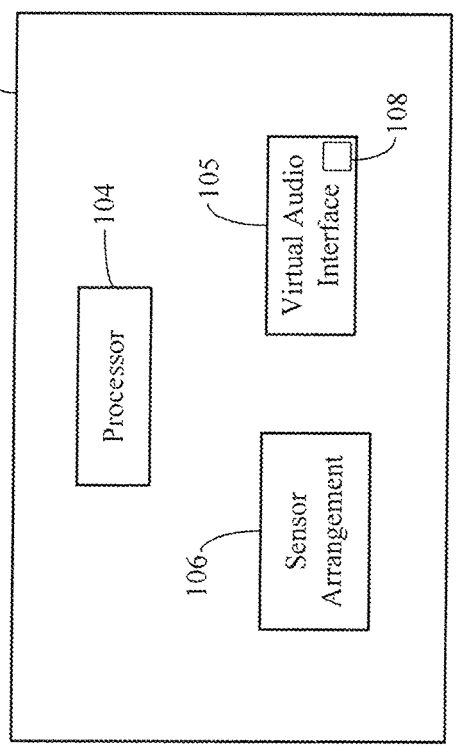
FIG. 1 illustrates a hearing assistance device that incorporates a virtual audio interface in accordance with various embodiments.

It is understood that the embodiments described herein may be used with any hearing assistance device without departing from the scope of this disclosure. The devices depicted in the figures are intended to demonstrate the subject matter, but not in a limited, exhaustive, or exclusive sense. It is also understood that the present subject matter can be used with a hearing assistance device designed for use in or on the right ear or the left ear or both ears of the wearer.

Hearing assistance devices, such as hearing aids and hearables (e.g., wearable earphones), typically include an enclosure, such as a housing or shell, within which internal components are disposed. Typical components of a hearing assistance device can include a digital signal processor (DSP), memory, power management circuitry, one or more communication devices (e.g., a radio, a near-field magnetic induction device), one or more antennas, one or more microphones, and a receiver/speaker, for example. More advanced hearing assistance devices can incorporate a long-range communication device, such as a Bluetooth® transceiver or other type of radio frequency (RF) transceiver.

Hearing assistance devices of the present disclosure can incorporate an antenna arrangement coupled to a high-frequency radio, such as a 2.4 GHz radio. The radio can conform to an IEEE 802.11 (e.g., WiFi®) or Bluetooth® (e.g., BLE, Bluetooth® 4.2 or 5.0) specification, for example. It is understood that hearing assistance devices of the present disclosure can employ other radios, such as a 900 MHz radio. Hearing assistance devices of the present disclosure can be configured to receive streaming audio (e.g., digital audio data or files) from an electronic or digital source. Representative electronic/digital sources (also referred to herein as accessory devices) include an assistive listening system, a TV streamer, a radio, a smartphone, a cell phone/entertainment device (CPED) or other electronic device that serves as a source of digital audio data or files.

The term hearing assistance device refers to a wide variety of devices that can aid a person with impaired hearing. The term hearing assistance device also refers to a wide variety of devices that can produce optimized or processed sound for persons with normal hearing. Hearing assistance devices of the present disclosure include hearables (e.g., wearable earphones, headphones, earbuds, virtual reality headsets), hearing aids (e.g., hearing instruments), cochlear implants, and bone-conduction devices, for example. Hearing assistance devices include, but are not limited to, behind-the-ear (BTE), in-the-ear (ITE), in-the-canal (ITC), invisible-in-canal (IIC), receiver-in-canal (RIC), receiver-in-the-ear (RITE) or completely-in-the-canal (CIC) type hearing assistance devices or some combination of the above. Throughout this disclosure, reference is made to a "hearing assistance device," which is understood to refer to a single hearing assistance device (for a single ear) or a pair of hearing assistance devices (one for each ear).

Embodiments of the disclosure are directed to hearing assistance devices that incorporate a virtual audio interface configured to guide the wearer of a hearing assistance device through a prescribed series of body movements or actions in accordance with a predetermined corrective or therapeutic maneuver, physical therapy or exercise routine. A maneuver, physical therapy or exercise routine involves a prescribed series of body movements or actions that can be implemented by the wearer of a hearing assistance device in an attempt to correct or treat a physiologic disorder or execute a physical fitness routine. The auditory guidance provided by the virtual audio interface can include any one or a combination of different sounds, such as tones, noise bursts, human speech, animal/natural sounds, synthesized sounds, and music, among other sounds.

In some embodiments, the virtual audio interface is configured to synthesize three-dimensional (3-D) audio that guides the wearer in performing specific physical movements of a predetermined corrective or therapeutic maneuver, physical therapy or exercise routine. According to some embodiments, the virtual audio interface can generate audio cues comprising spatialized 3-D virtual sound emanating from virtual spatial locations that serve as targets for guiding wearer movement. The wearer can execute a series of body movements in a direction and/or extent indicated by a sequence of virtual sound targets. The sound generated at the virtual spatial locations can be any broadband sound, such as complex tones, noise bursts, human speech, music, etc. or a combination of these and other types of sound. In various embodiments, the virtual audio interface is configured to generate binaural or monaural sounds, alone or in combination with spatialized 3-D virtual sounds. The binaural and monaural sounds can be any of those listed above including single-frequency tones.

In other embodiments, the virtual audio interface is configured to generate human speech that guides the wearer in performing specific physical movements of a predetermined corrective or therapeutic maneuver, physical therapy or exercise routine. The speech can be synthesized speech or a pre-recording of real speech. In embodiments that employ a single hearing assistance device (for one ear), for example, the virtual audio interface generates monaural sound in the form of speech, which can be accompanied by other sounds, such as single or multi-frequency tones, noise bursts or music. In embodiments that employ two hearing assistance devices (one device for each ear), the virtual audio interface can generate monaural or binaural sound in the form of speech, which can be accompanied by other sounds, such as single or multi-frequency tones, noise bursts or music. The virtual audio interface can display (play back) spoken instructions to guide the wearer though specific physical movements of a predetermined corrective or therapeutic maneuver, physical therapy or exercise routine.

According to further embodiments, the virtual audio interface is configured to generate both human speech (e.g., synthesized or real) and non-speech sounds. The virtual audio interface can, for example, generate both speech and synthesized 3-D audio that together guide the wearer in performing specific physical movements of a predetermined corrective or therapeutic maneuver, physical therapy or exercise routine. For example, the virtual audio interface can display spoken words that instruct the wearer to assume a specific position, such as lying down, standing or sitting up. A spoken instruction can be displayed that requests the wearer to move a specific body part in a particular manner. For example, the wearer can be instructed to turn his or her head by approximately 45° to the right (e.g., "turn your head so your nose is pointing 45° to the right"). A synthesized 3-D virtual audio target can be generated at the specified location relative to the wearer's current head position. In response, the wearer moves his or her head in the specified direction indicated by the audio target.

According to various embodiments, a hearing assistance device that incorporates a virtual audio interface also incorporates a sensor arrangement configured to sense movement of the wearer during each of the body actions required to implement a predetermined corrective or therapeutic maneuver, physical therapy or exercise routine. The sensor arrangement can comprise one or a multiplicity of sensors, such one or more of an inertial measurement unit (IMU), accelerometer, gyroscope, magnetometer, and eye movement sensor (e.g., electrooculogram (EOG) sensor). In some embodiments, the sensor arrangement can comprise one or more additional sensors that are external of the hearing assistance device. The one or more additional sensors can comprise one or more of an IMU, accelerometer, gyroscope, magnetometer, heart rate monitor, and pulse oximeter. For example, the one or more additional sensors can include a wrist-worn or ankle-worn sensor arrangement or a sensor arrangement supported by a chest strap.

The sensor arrangement of a hearing assistance device is configured to sense movement of the wearer as he or she executes each action of a predetermined corrective or therapeutic maneuver, physical therapy or exercise routine. Data produced by the sensor arrangement is operated on by a processor of the hearing assistance device to determine if a specified action was successfully or unsuccessfully executed by the wearer. The virtual audio interface can generate an audio output indicating success or lack of success of each or a series of specified actions.

Alternatively or in addition, the virtual audio interface can generate an electrical signal output indicating success or lack of success of each or a series of specified bodily actions. The signal output can be transmitted from the hearing assistance device to an external device, such as a wrist-worn electronic device (e.g., a smart watch), smartphone, tablet, laptop or other electronic device. In response to the signal output, the external device can generate an output indicating success or lack of success of each or a series of specified actions. Corrective feedback can also be generated by the external device. The output produced by the external device can be one or a combination of a visual, auditory (e.g., sounds and/or speech) or tactile output. The signal output can also be stored in a memory internal to or external of the hearing assistance device (e.g., a memory of an external device). The stored signal output, which can include other data associated with the predetermined maneuver, physical therapy or exercise routine, can be transmitted from the hearing assistance device and/or external device to a remote server. The associated data can include one or more of the name of the maneuver/therapy/routine, time and date of execution, and wearer ID information, for example. The remote server can store such data acquired from a multiplicity of wearers.

FIG. 1 illustrates a hearing assistance device that incorporates a virtual audio interface 105 in accordance with various embodiments. The hearing assistance device 102 shown in FIG. 1 includes a processor 104 coupled to the virtual audio interface 105 and a sensor arrangement 106. In some embodiments, the processor 104 of the hearing assistance device 102 is configured to implement the virtual audio interface 105. In other embodiments, the virtual audio interface 105 incorporates its own processor or logic circuit and cooperates with the processor 104 during operation. For simplicity of explanation, reference is made to the processor 104 in the following discussion, which can be a processor of the virtual audio interface 105 or a processor of the hearing assistance device. The virtual audio interface 105 includes or is coupled to a speaker 108. It is understood that the hearing assistance device 102 typically includes other components (see, e.g., FIGS. 3 and 4).

According to various embodiments, the virtual audio interface 105, via processor 104 or a separate processor, is configured to generate a sequence of audio cues that audibly guide a wearer of the hearing assistance device 102 through a series of actions involving one or more body parts in accordance with a predetermined corrective or therapeutic maneuver, physical therapy or exercise routine. The speaker 108 is configured to play back the sequence of audio cues for reception by the wearer. The sensor arrangement 106 comprises one or more sensors configured to sense movement of a body part during each of the actions. The processor 104 is configured to determine if movement of a body part for an action associated with each audio cue has been correctly executed by the wearer. The processor 104 is configured to produce an output indicative of successful or unsuccessful execution of the actions by the wearer.

Figure 2:
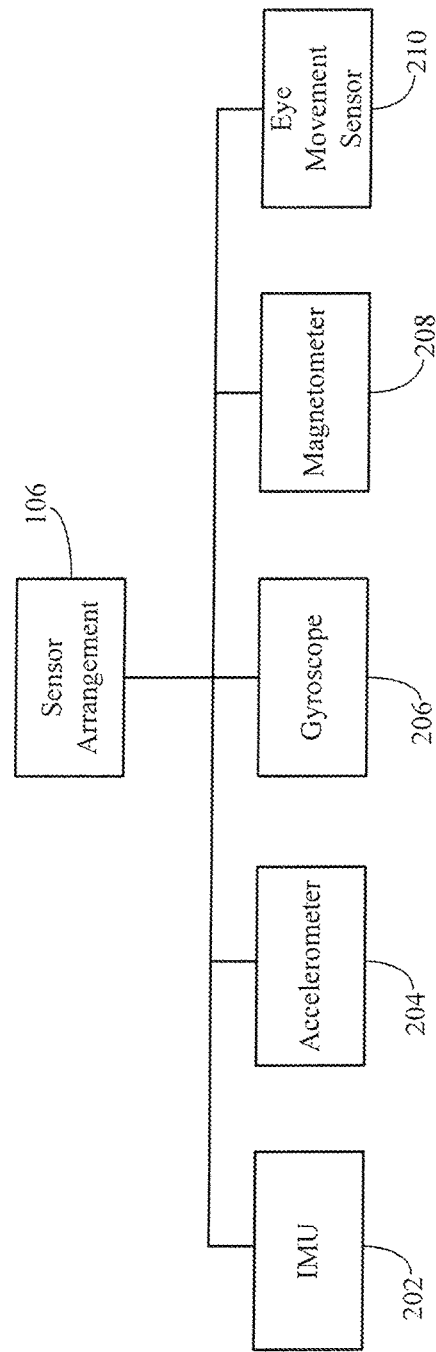
FIG. 2 illustrates a sensor arrangement of the hearing assistance device shown in FIG. 1.

The sensor arrangement 106 can comprise one or more sensors, such as those shown in FIG. 2. According to various embodiments, the sensor arrangement 106 can include one or more of an IMU 202, and accelerometer 204, a gyroscope 206, a magnetometer 208, and an eye movement sensor 210. The IMU 202 can be of a type disclosed in commonly owned U.S. patent application Ser. No. 15/331,230, filed Oct. 21, 2016, which is incorporated herein by reference. The eye movement sensor 210 may be, for example, an electrooculographic (EOG) sensor, such as an EOG sensor disclosed in commonly owned U.S. Pat. No. 9,167,356, which is incorporated herein by reference. In some embodiments, such as when conducting a therapy at a clinic, eye movement can be manually characterized. In other embodiments, eye movement can be captured and characterized using a camera (e.g., of a smartphone or smart-glasses) in cooperation with an app (e.g., executed by the smartphone or smart-glasses), such as in the manner described in US 2007/0177103, which is incorporated herein by reference. As was discussed previously, the sensor arrangement 106 can include one or more sensors that are external to the hearing assistance device 102. In addition to the external sensors discussed hereinabove, the sensor arrangement 106 can comprise a network of body sensors (such as those listed above) that sense movement of a multiplicity of body parts (e.g., arms, legs, torso).

The virtual audio interface implemented by the processor 104 can be configured to guide the wearer of a hearing assistance device through actions for correcting Benign Paroxysmal Positional Vertigo (BPPV) or actions of a vestibular rehabilitation therapy. These conditions can be corrected by performing very specific head actions that together define a corrective or therapeutic maneuver (e.g., the Epley maneuver). Such therapeutic maneuvers, however, can be very difficult for individuals to learn or perform alone. Presently, audiologist and physical therapists may choose to teach their patients how to perform the maneuvers to reduce visits, but the maneuvers themselves are not intuitive.

Traditionally, therapies for correcting BPPV and other vestibular disorders require the patient to make repeated visits to their health care professionals (e.g., audiologist or physical therapist) for assistance in performing these therapies. The quality of at-home physical therapy activities are significantly improved with the greater degree of guidance provided by a virtual audio interface of the present disclosure. The audio guidance provided by the virtual audio interface of a hearing assistance device can eliminate the need for additional appointments with a health professional. This saves the patient time, money, and frustration. This also allows a health professional to increase his or her patient base while enhancing professional oversight and improving patient compliance and outcomes.

According to some embodiments, correcting for BPPV and other vestibular disorders involves generating, by the hearing assistance device 102, a sequence of audio cues that audibly guide the wearer through a series of predefined actions involving the wearer's head and neck. In some embodiments, the sequence of audio cues comprises a sequence of spoken instructions played back by the hearing assistance device 102. In other embodiments, the sequence of audio cues comprises synthesized 3-D audio sounds, such as virtual audio targets, that allow the wearer to literally follow an auditory object through a particular maneuver (e.g., the wearer points his or her nose to the targets and follows the targets). By following the path of the auditory object, the wearer correctly performs the prescribed physical maneuver. Using one or more sensors of the sensor arrangement 106, the hearing assistance device 102 senses movement of the head during each action of a maneuver. The processor 104 determines if head movement for an action associated with each audio cue has been correctly executed by the wearer. The processor 104 is configured to produce an output indicating whether or not the wearer successfully executed the actions. The processor 104 can produce the output indicative of successful or unsuccessful execution of a single action of a maneuver, a series of actions of the maneuver, or the entire maneuver.

Figure 3:
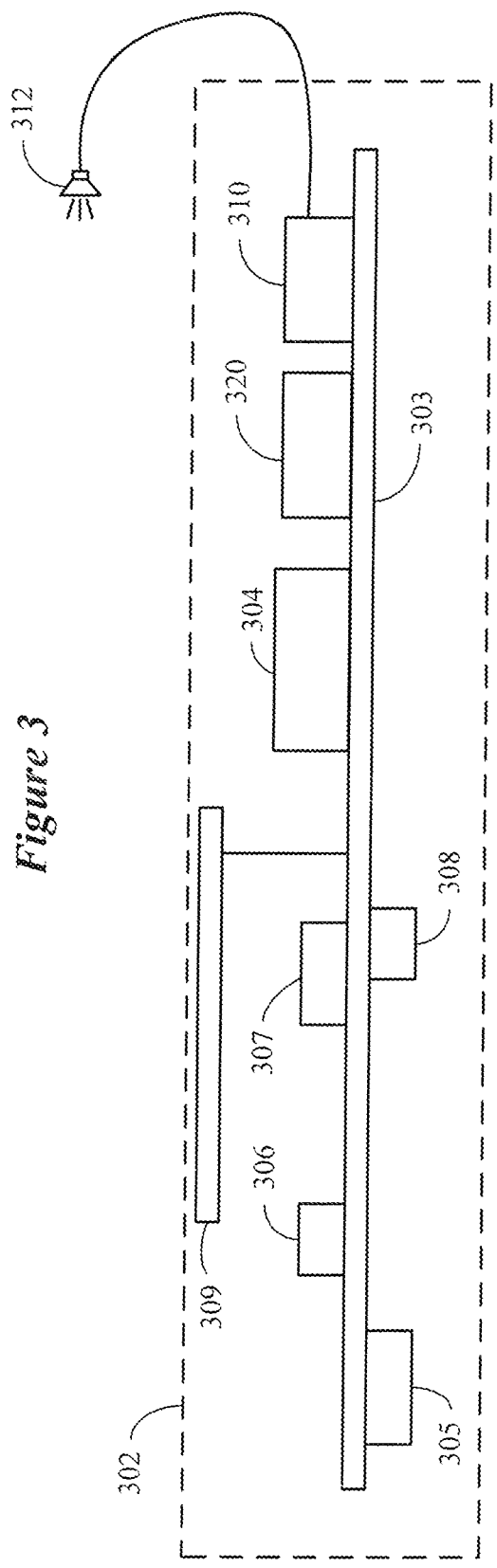
FIG. 3 is a block diagram showing various components of a hearing assistance device that can be configured to implement a virtual audio interface in accordance with various embodiments.

FIG. 3 is a block diagram showing various components of a hearing assistance device that can be configured to implement a virtual audio interface in accordance with various embodiments. The block diagram of FIG. 3 represents a generic hearing assistance device for purposes of illustration. The hearing assistance device 302 shown in FIG. 3 includes several components electrically connected to a mother flexible circuit 303. A battery 305 is electrically connected to the mother flexible circuit 303 and provides power to the various components of the hearing assistance device 302. One or more microphones 306 are electrically connected to the mother flexible circuit 303, which provides electrical communication between the microphones 306 and a digital signal processor (DSP) 304. Among other components, the DSP 304 incorporates or is coupled to audio signal processing circuitry configured to implement a virtual audio interface of the disclosure. A sensor arrangement 320 is coupled to the DSP 304 via the mother flexible circuit 303. One or more user switches 308 (e.g., on/off, volume, mic directional settings) are electrically coupled to the DSP 304 via the flexible mother circuit 303.

An audio output device 310 is electrically connected to the DSP 304 via the flexible mother circuit 303. In some embodiments, the audio output device 310 comprises a speaker (coupled to an amplifier). In other embodiments, the audio output device 310 comprises an amplifier coupled to an external receiver 312 adapted for positioning within an ear of a wearer. The hearing assistance device 302 may incorporate a communication device 307 coupled to the flexible mother circuit 303 and to an antenna 309 directly or indirectly via the flexible mother circuit 303. The communication device 307 can be a Bluetooth® transceiver, such as a BLE (Bluetooth® low energy) transceiver or other transceiver (e.g., an IEEE 802.11 compliant device). The communication device 307 can be configured to communicate with one or more external devices, such as those discussed previously, in accordance with various embodiments.

Figure 4:
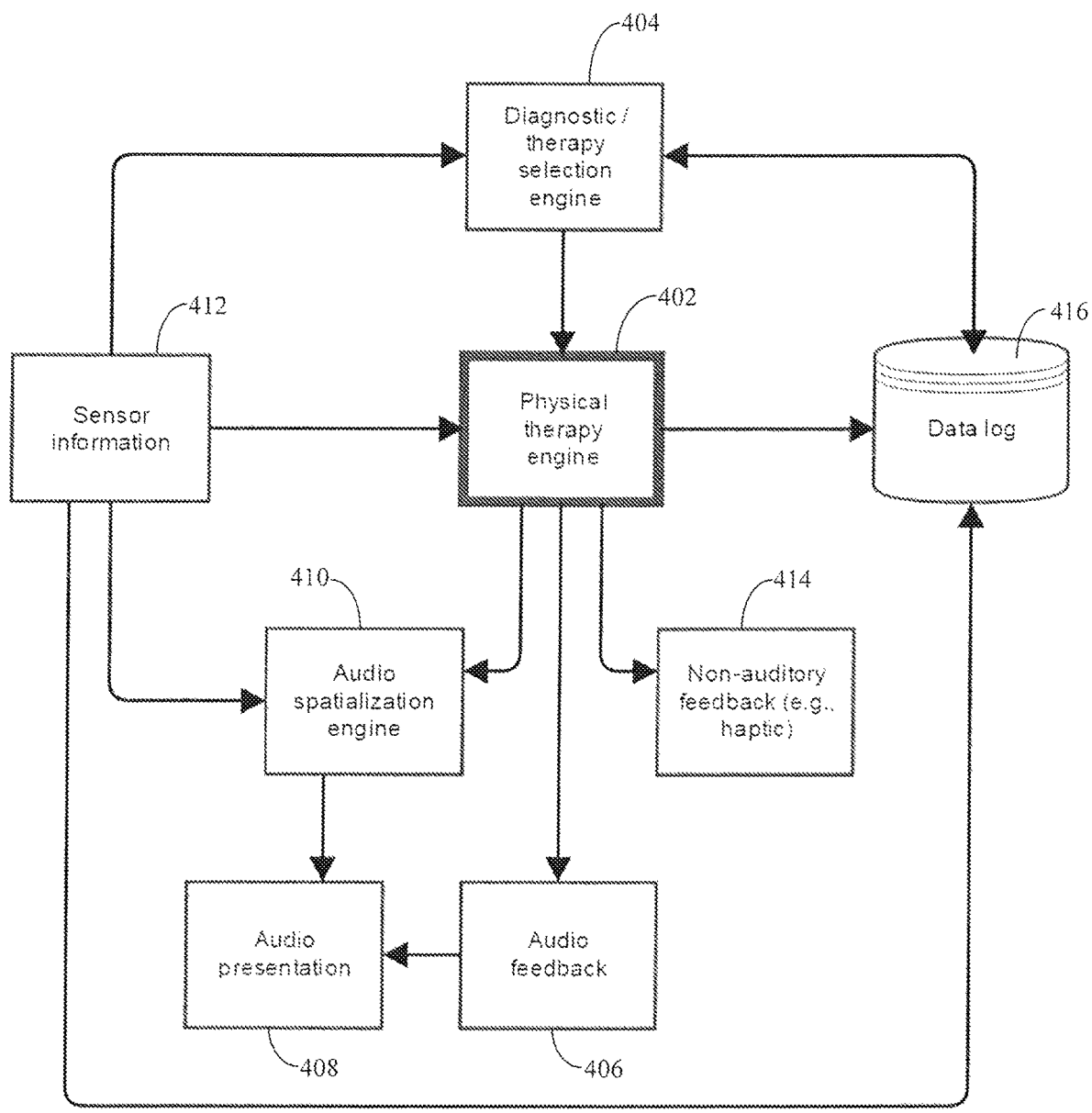
FIG. 4 is a block diagram showing components and features of a hearing assistance device that incorporates a virtual audio interface in accordance with various embodiments.

According to various embodiments, the hearing assistance devices shown in FIGS. 1 and 3 can incorporate the components and features shown in FIG. 4. A hearing assistance device can to include a physical therapy engine 402 configured to audibly guide a wearer of the hearing assistance device through a series of actions associated with one or more predetermined physical therapies or corrective/therapeutic maneuvers. In some embodiments, the physical therapy engine 402 is configured to implement a multiplicity of different therapies and receives an input from a selection engine 404. The selection engine 404 allows selection of one of several different therapies by the wearer (or healthcare professional) in response to a selection input. The selection input can be a voice input, an input using a user switch of the hearing assistance device, or an input received from a smartphone or other external device. In some embodiments, sensor information 412 (e.g., from an eye movement sensor) can indicate presence of a vestibular disturbance (e.g., BPPV). In response to detecting the vestibular disturbance, an audio message can be communicated to the wearer that a corrective therapy should be performed as soon as possible. The selection engine 404 can select an appropriate therapy for execution by the physical therapy engine 402 at an appropriate time.

The physical therapy engine 402, together with other elements of FIG. 4, guides the wearer through a series of actions involving one or more body parts via a sequence of audio cues in accordance with the selected maneuver/therapy/routine indicated by the selection engine 404. Audibly guiding the wearer through a series of action can involve generating stationary or moving virtual audio targets by an audio spatialization engine 410. As the wearer executes each action, the physical therapy engine 402 receives sensor information 412 and determines whether the wearer successfully or unsuccessfully executed each of the actions.

During the therapy, audio feedback 406 is provided to the wearer. The audio feedback 406 can include speech, tones, music or other sounds that aid the wearer in executing each action and provide feedback as to the wearer's success or lack of success in executing each action. Non-auditory feedback 414 (e.g., tactile, such as vibration) 414 can also be provided to the wearer. The audio feedback 406 and virtual audio targets produced by the audio spatialization engine 410 are presented 408 to the wearer at the appropriate time under the control of the physical therapy engine 402. It is noted that some or all of blocks 402, 406, 408, 410, and 414 may be considered elements of a virtual audio interface according to various embodiments. A data log 416 can receive data from the physical therapy engine 402, sensor information 412, and selected therapy information from the therapy selection engine 404. The data log 416 can be supported by a memory of the hearing assistance device, a memory of an external device, or a memory of a remote server, for example. Data stored in the data log 416 can be used to improve the operation of the virtual audio interface of the hearing assistance device.

A virtual audio interface can incorporate selected elements shown in FIG. 4 according to various embodiments. It is to be understood that some embodiments of a virtual audio interface exclude one or more of the elements shown in FIG. 4. For example, a virtual audio interface can exclude the audio spatialization engine 410 according to some embodiments. Instead, an audio engine that produces binaural or monaural sound can replace the audio spatialization engine 410. In other embodiments, a virtual audio interface can exclude non-auditory feedback 414.

Figure 5:
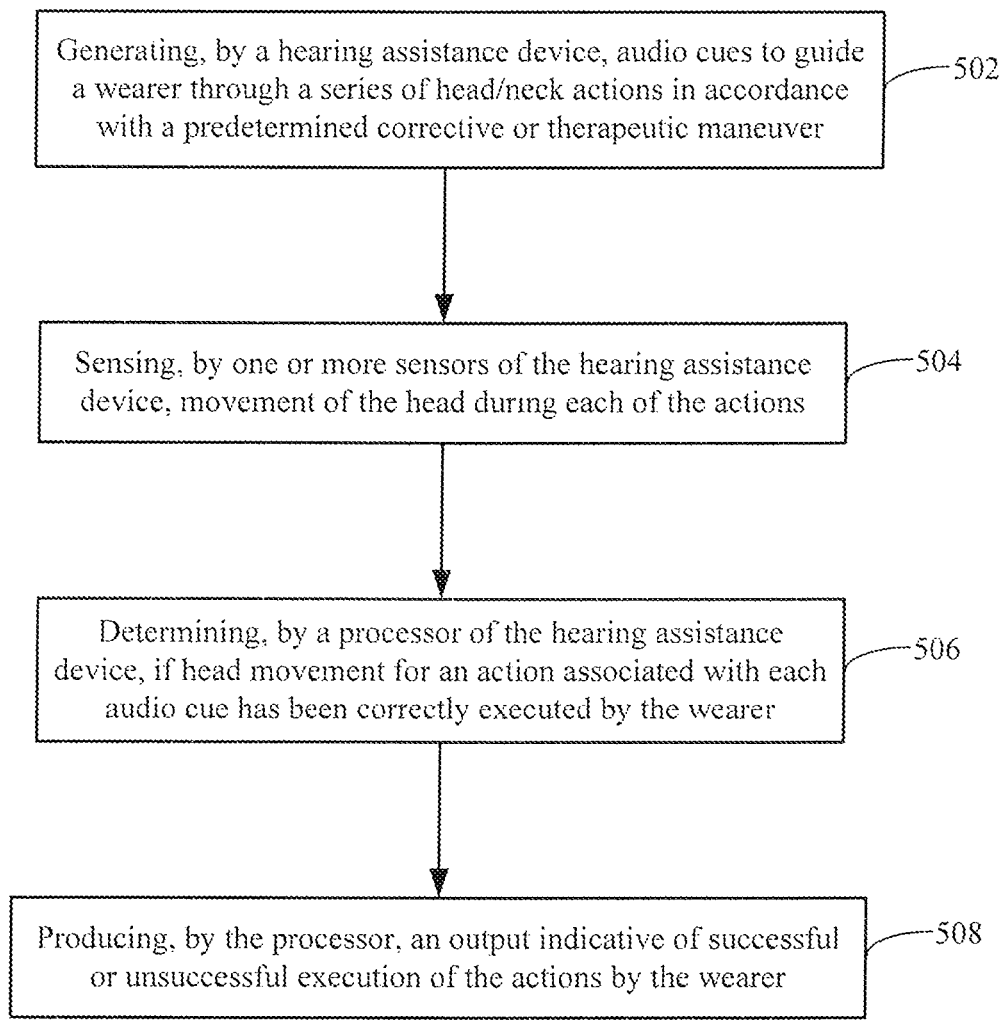
FIG. 5 is a flow chart showing various processes performed by a hearing assistance device that includes a virtual audio interface in accordance with various embodiments.

FIG. 5 is a flow chart showing various processes performed by a hearing assistance device that includes a virtual audio interface in accordance with various embodiments. According to FIG. 5, the virtual audio interface is configured to audibly guide a wearer of the hearing assistance device through a series of actions involving the wearer's head and neck. The head and neck actions can be part of a predetermined corrective or therapeutic maneuver or physical therapy. In some embodiments, the head and neck actions can be part of a predefined exercise or fitness routine. The maneuver, therapy or exercise routine can be any therapy that involves the head and neck, such as a vestibular rehabilitation therapy or therapy to strengthen the neck or spine after surgery or an injury. It is understood that the physical therapy can involve parts of the body other than, or in addition to, the head or neck.

The method illustrated in FIG. 5 involves generating 502, by a hearing assistance device, audio cues (e.g., prompts) to guide a wearer through a series of head and neck actions in accordance with a predetermined corrective or therapeutic maneuver. The method also involves sensing 504, by one or more sensors of the hearing assistance device, movement of the head during each of the actions. The method further involves determining 506, by a processor of the hearing assistance device, if head movement for an action associated with each audio cue has been correctly executed by the wearer. The method also involves producing 508, by the processor, an output indicative of successful or unsuccessful execution of the actions by the wearer.

Figure 6:
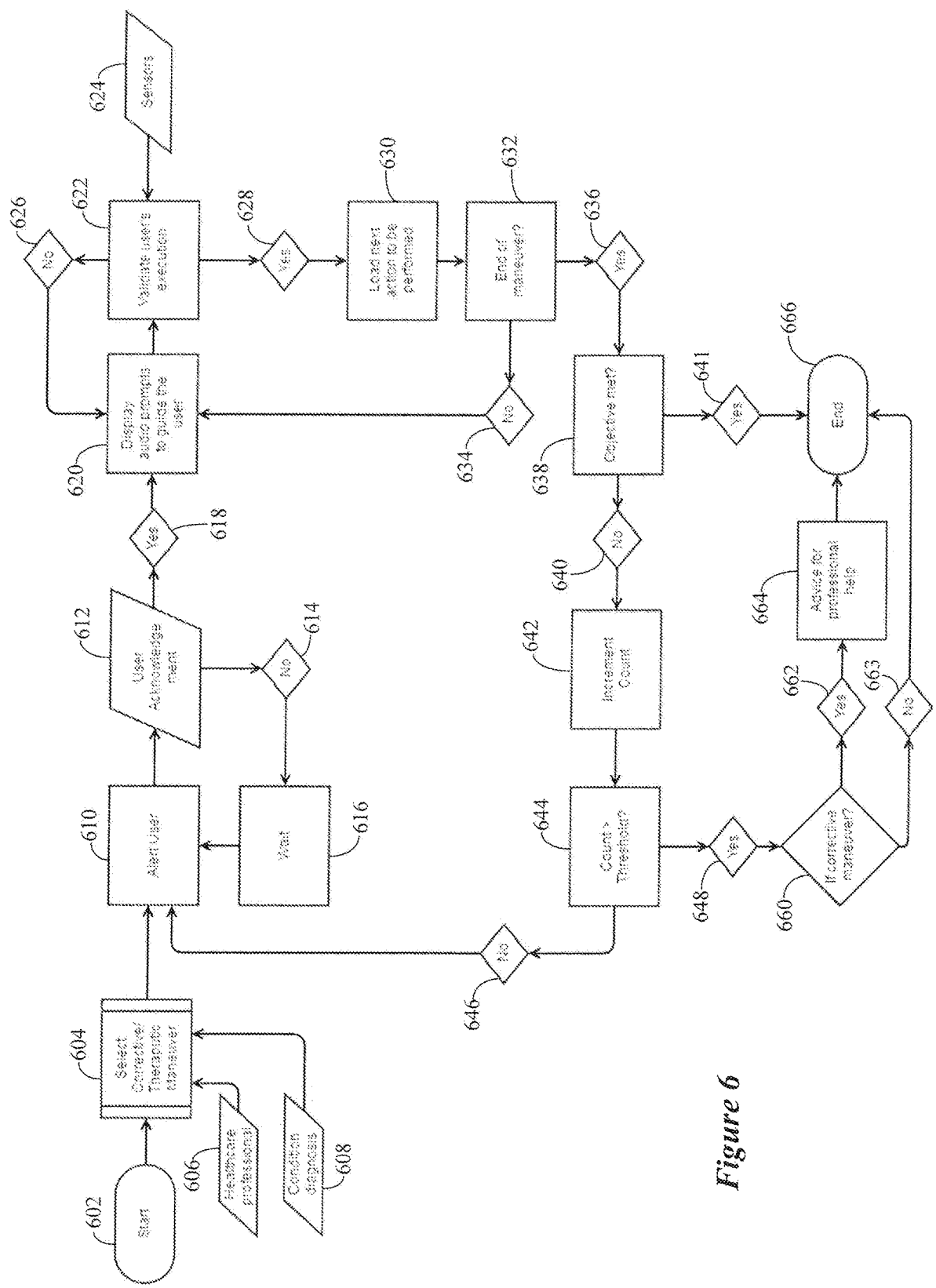
FIG. 6 is a flow chart showing various processes performed by a hearing assistance device that includes a virtual audio interface in accordance with various embodiments.

FIG. 6 is a flow chart showing various processes performed by a hearing assistance device that includes a virtual audio interface in accordance with various embodiments. The processes shown in FIG. 6 audibly guide a wearer of the hearing assistance device through a series of actions involving one or more body parts in accordance with a predefined corrective or therapeutic maneuver. At the start 602 of the processes shown in FIG. 6, it is assumed that a wearer is equipped with a hearing assistance device that, in general terms, generates sound and couples the sound to one or both of the wearer's ears.

A corrective or therapeutic maneuver can be selected 604 by a healthcare professional 606 or the wearer of the hearing assistance device. Selection of a corrective or therapeutic maneuver 604 can be effected by a voice command, activation of a switch on the hearing assistance device, or a wireless signal generated by an external device such as a smartphone, tablet or laptop, for example. In some embodiments, a memory of the hearing assistance device can store several different corrective or therapeutic maneuver programs for selection 604. In other embodiments, an external device can store several different corrective or therapeutic maneuver programs, and a desired program can be selected 604 by the healthcare professional 606 or the wearer and uploaded to the hearing assistance device. The corrective or therapeutic maneuver programs can be uploaded in batch or via streaming to the hearing assistance device. For example, audio cues of a program stored on the external device can be transmitted (e.g., streamed) to the hearing assistance device in real-time during execution of the program by the hearing assistance device.

In some embodiments, the hearing assistance device is equipped with one or more sensors that can diagnose a physiologic condition of the wearer. For example, an eye movement sensor of the hearing assistance device can sense nystagmus indicative of dizziness or vertigo. A motion sensor (e.g., IMU, accelerometer, gyroscope, magnetometer, eye movement sensor) of the hearing assistance device can detect stumbling or falling by the wearer and, in addition or alternatively, be used to monitor the vestibular system, such as in accordance with commonly owned U.S. Provisional Patent Application Ser. No. 62/458,436, filed on Feb. 13, 2017 ("Hearing Assistance System and Method Using Same"), which is incorporated herein by reference. A therapeutic maneuver 604 can be selected automatically by the hearing assistance device to treat the diagnosed condition 608. Prior to initiating the therapeutic maneuver 604, the hearing assistance device can verify through audio interaction with the wearer whether or not the diagnosed condition 608 is accurate.

Following selection of a corrective or therapeutic maneuver 604, the wearer is alerted 610 that the maneuver will be commencing. The hearing assistance device awaits an acknowledgment 612 from the user prior to commencing. The acknowledgment can be in the form of a verbal input, a switch input, or an external device input. If an acknowledgement is not received 614, the hearing assistance device waits 616 for a predetermined period of time (e.g., one minute). If the predetermined period of time expires without receiving an acknowledgment, the wearer can be alerted 610 that the selected maneuver 604 has been canceled, thereby ending 666 the processes shown in FIG. 6.

If an acknowledgment 612 is affirmatively received 618, audio prompts are displayed (played back) 620 that guide the wearer to move a specified body part through a particular action of the maneuver. The audio prompts can be in the form of speech, sounds, or combination of speech and sounds. For example, the audio prompts can be spatialized virtual sound targets (stationary or moving) that the wearer can follow when executing a particular action. One or more sensors 624 of the hearing assistance device sense movement of the specified body part, and the hearing assistance device validates 622 execution of the particular action of the maneuver. If the hearing assistance device determines that the wearer unsuccessfully executed the particular action, as indicated by the No block 626, audio prompts are displayed 622 to assist the wearer in repeating the particular action of the maneuver. In response to successfully executing the particular action, as indicated by the Yes block 628, the next action to be performance is loaded for execution 630. If the end of the maneuver 632 has not been reached, as indicated by the No block 634, audio prompts are displayed 620 that guide the wearer to move a specified body part through the next action of the maneuver to be performed. The processes shown in blocks 620-634 are repeated for each additional action of the maneuver until the end of the maneuver 632 has been reached, as indicated by the Yes block 636.

The hearing assistance device performs a check to determine if the objective of the corrective or therapeutic maneuver has been met 638. If the objective of the corrective or therapeutic maneuver has been met, as indicated by the yes block 641, the processes shown in FIG. 6 are terminated 666. If not met 640, a counter is incremented 642 and compared against a count threshold. The count threshold can correspond to a predetermined number of attempts that can be made to execute the selected corrective or therapeutic maneuver 604 (e.g., the count threshold can be set to 2 or 3). If the count does not exceed the count threshold 644, as indicated by the No block 646, the processes of blocks 610-644 are repeated.

If the count exceeds the count threshold 644, as indicated by the Yes block 648, a check is made 660 to determine if the maneuver 604 is a corrective maneuver. If the maneuver 604 is not a corrective maneuver, as indicated by the No block 663, the processes shown in FIG. 6 are terminated 666. If the maneuver 604 is a corrective maneuver, as indicated by the Yes block 662, the hearing assistance device can advise the wearer to seek professional advice or assistance 664, after which the processes shown in FIG. 6 are terminated 666.

FIG. 7 is a flow chart showing various processes performed by a hearing assistance device that includes a virtual audio interface in accordance with various embodiments. In the embodiment shown in FIG. 7, the virtual audio interface is configured to generate verbal cues or prompts that guide a wearer of the hearing device assistance device through a series of actions associated with a corrective maneuver known as the Epley maneuver. The Epley maneuver is a series of head and neck actions used to treat BPPV. The processes shown in FIG. 7 are particularly useful when implemented in a monaural hearing assistance device configured for use with a single ear.

At block 702, the hearing assistance device initiates 702 an Epley maneuver guidance program. The virtual audio interface of the hearing assistance device displays audio cue 704: "While lying on a flat surface, place a pillow under your shoulder so your neck extends over the pillow. Then sit up." The hearing assistance device (e.g., processor and sensor(s)) performs a sensor check 706 to determine if the wearer of the hearing assistance device performed to required action successfully (referred to in subsequent blocks as a sensor check). The virtual audio interface can generate a verbal comment 708 indicating whether the wearer successfully or unsuccessfully performed the required action. If unsuccessfully performed, the virtual audio interface can generate a verbal comment 708 requesting the wearer to repeat the required action (e.g., repeating audio cue 704). For brevity, these verbal comments are collectively referred to in subsequent blocks as a verbal comment. The virtual audio interface displays audio cue 710: "While looking forward, turn your head toward the affected ear so your chin approaches the shoulder." A sensor check is performed 712 and a verbal comment 714 is generated, as previously described.

The virtual audio interface displays audio cue 716: "With your head turned, lie back rather quickly while looking straight. Hold this position for one minute or longer if you experience spinning." The hearing assistance device initiates a timer for one minute and performs a sensor check 718, and generates a verbal comment 720. An eye movement sensor of the hearing assistance device can be used to sense for nystagmus, which can confirm the wearer's experience of spinning when lying back quickly in response to audio cue 716. The hearing assistance device can record 722 the presence of benign positional vertigo for the affected ear in response to sensing nystagmus. This and other data associated with execution of the Epley maneuver guidance program can be uploaded to a remote server accessible by healthcare professionals (e.g., transferred to the data log 416 shown in FIG. 4).

The virtual audio interface displays audio cue 724: "Turn your head to the other side toward your unaffected ear. Hold this position for at least one minute." The hearing assistance device initiates a timer for one minute and performs a sensor check 726, and generates a verbal comment 728. The virtual audio interface displays audio cue 730: "Roll up on your shoulder so you are sideways with your chin tucked down toward your shoulder and your nose pointed down at a 45° angle between the flat surface and the wall. Hold this position for at least one minute." The hearing assistance device initiates a timer for one minute and performs a sensor check 732, and generates a verbal comment 734. The eye movement sensor can be used to sense for nystagmus which can occur from movement responsive to audio cue 730. The hearing assistance device can record 736 the presence of benign positional vertigo for the affected ear in response to sensing nystagmus.

The virtual audio interface displays audio cue 738: "Sit up with your head in the same position, with your chin tucked down toward your shoulder." The hearing assistance device performs a sensor check 740 and generates a verbal comment 742. The virtual audio interface displays audio cue 744: "Slowly straighten out your head and look forward. Wait 30 seconds after which the therapy is concluded." The hearing assistance device initiates a timer for 30 seconds and performs a sensor check 746, and generates a verbal comment 748. The eye movement sensor can be used to sense for nystagmus which can occur from movement responsive to audio cue 744. The hearing assistance device can record 750 the presence of benign positional vertigo for the affected ear in response to sensing nystagmus. At block 752, audio cue 752 is displayed to indicate to the wearer that the Epley maneuver guidance program has been completed.

Figure 8A:
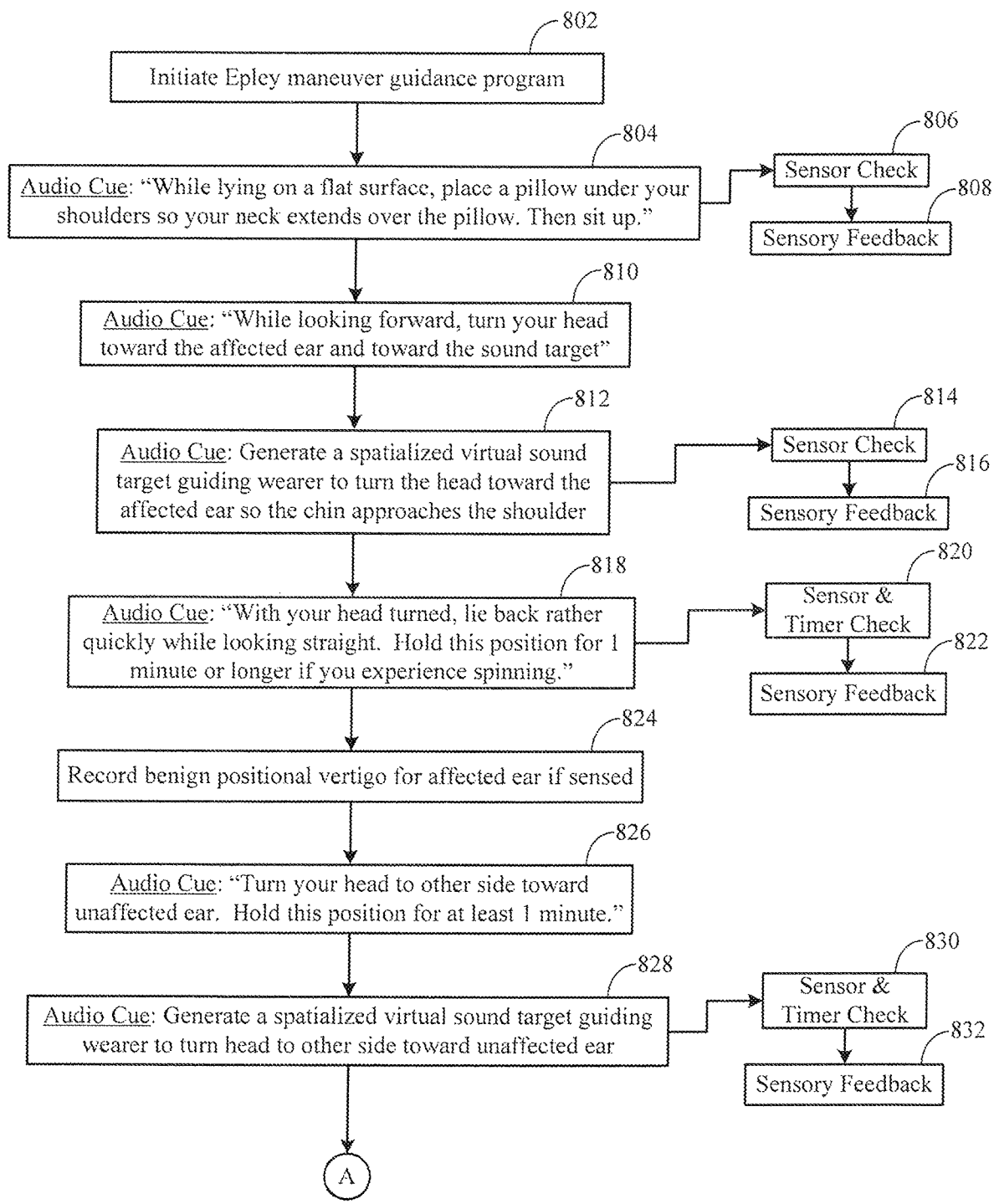
FIGS. 8A and 8B are flow charts showing various processes performed by a hearing assistance device that includes a virtual audio interface in accordance with various embodiments.
Figure 8B:
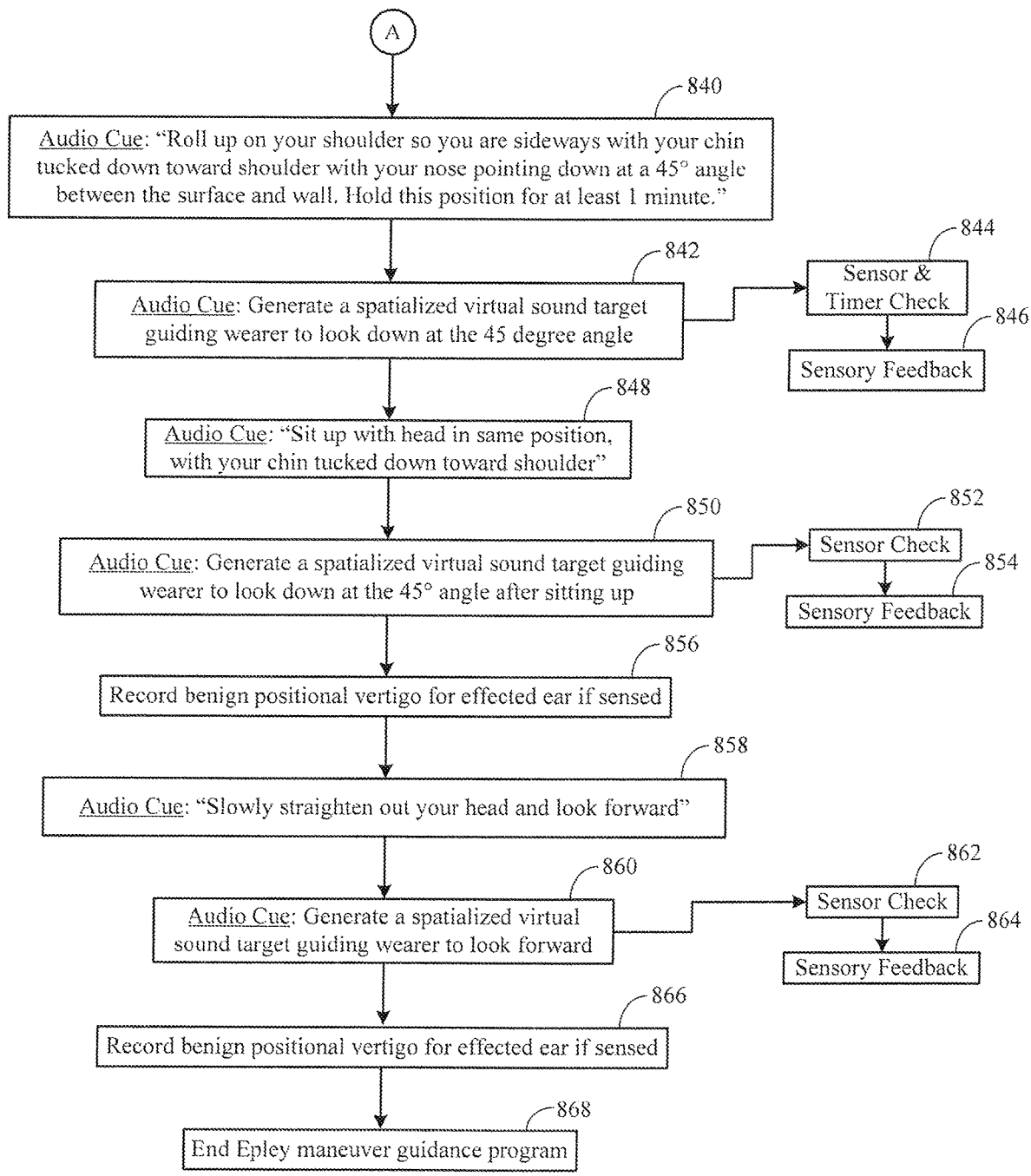

FIGS. 8A and 8B are flow charts showing various processes performed by a hearing assistance device that includes a virtual audio interface in accordance with various embodiments. In the embodiment shown in FIGS. 8A and 8B, the virtual audio interface is configured to generate verbal cues/prompts and spatialized 3-D virtual sound that guide a wearer of the hearing device assistance device through a series of actions associated with the Epley maneuver. The processes shown in FIGS. 8A and 8B are particularly useful when implemented in a binaural hearing assistance device configured for use with both ears.

At block 802, the hearing assistance device initiates an Epley maneuver guidance program. The virtual audio interface of the hearing assistance device displays audio cue 804: "While lying on a flat surface, place a pillow under your shoulder so your neck extends over the pillow. Then sit up." The hearing assistance device (e.g., processor and sensor(s)) performs a sensor check 806 to determine if the wearer of the hearing assistance device performed to required action successfully (referred to in subsequent blocks as a sensor check). The virtual audio interface can generate sensory feedback 808 indicating whether the wearer successfully or unsuccessfully performed the required action. The sensory feedback can be one or a combination of spoken words, tones, noise bursts, music, and tactile (e.g., vibration) feedback. The sensory feedback can also be visual, audio, or tactile feedback via an app running on a smartphone. If unsuccessfully performed, the virtual audio interface can generate sensory feedback 808 indicating that the wearer needs to repeat the required action. For brevity, the sensory feedback generated in response to performing and repeating the required action is referred to collectively in subsequent blocks as sensor feedback.

The virtual audio interface displays audio cue 810: "While looking forward, turn your head toward the affected ear and towards the sound target." After generating the audio cue 810, the hearing assistance device generates 812 a spatialized virtual sound target which guides the wearer to turn his or her head toward the affected ear so that the chin approaches the shoulder. The spatialized virtual sound target can be a stationary or moving sound target. The hearing assistance device performs a sensor check 814 and generates sensory feedback 816. The virtual audio interface displays audio cue 818: "With your head turned, lie back rather quickly while looking straight. Hold this position for one minute or longer if you experience spinning." The hearing assistance device initiates a timer for one minute and performs a sensor check 820, and generates sensory feedback 822. An eye movement sensor of the hearing assistance device can be used to sense for nystagmus which can occur due to movement responsive to audio cue 818. The hearing assistance device can record 824 the presence of benign positional vertigo for the affected ear in response to sensing nystagmus. The hearing assistance device displays audio cue 826: "Turn your head to the other side toward the unaffected ear. Hold this position for at least one minute." After generating the audio cue 826, the hearing assistance device generates 828 a spatialized virtual sound target (stationary or moving) guiding the wearer to turn his or her head to the other side toward the unaffected ear. The hearing assistance device initiates a timer for one minute and performs a sensor check 830, and generates sensory feedback 832.

The hearing assistance device displays audio cue 840: "Roll up on your shoulder so you are sideways with your chin tucked down toward the shoulder with your nose pointing down at a 45° angle between the flat surface and wall." After generating the audio cue 840, the hearing assistance device generates 842 a spatialized virtual sound target (stationary or moving) guiding the wearer to look down at the 45° angle. The hearing assistance device initiates a timer for one minute and performs a sensor check 844, and generates sensory feedback 846. The hearing assistance device displays audio cue 848: "Sit up with your head in the same position, with your chin tucked down towards your shoulder." After generating the audio cue 848, the hearing assistance device generates 850 a spatial virtual sound target (stationary or moving) guiding the wearer to look down at the 45° angle after sitting up. The hearing assistance device performs a sensor check 852 and generates sensory feedback 854. The eye movement sensor can be used to sense for nystagmus which can occur due to movement responsive to audio cue 848. The hearing assistance device can record 856 the presence of benign positional vertigo for the affected ear in response to sensing nystagmus. The hearing assistance device displays audio cue 858: "Slowly straighten out your head and look forward." After generating the audio cue 858, the hearing assistance device generates 860 a spatialized virtual sound target (stationary or moving) guiding the wearer to look forward. The hearing assistance device performs a sensor check 862 and generates sensory feedback 864. The eye movement sensor can be used to sense for nystagmus which can occur from movement responsive to audio cue 858. The hearing assistance device can record 866 the presence of benign positional vertigo for the affected ear in response to sensing nystagmus. At block 868, the Epley maneuver guidance program is terminated. Data associated with execution of the Epley maneuver guidance program can be communicated to a remote server accessible by a healthcare provider, as previously discussed.

After performing the Epley maneuver according to the techniques discussed herein, the wearer of the hearing assistance device can be reminded that they should not be driving for a prescribed period of time (e.g., 24 hour limitation). According to some embodiments, the hearing assistance device can be configured to sense if the wearer is in the car during the prescribed period of time (via a timer function of the hearing assistance device). For example, an accelerometer and the hearing assistance device environment or activity detection (which could be derived from acoustic and/or other sensors in the hearing assistance device) can sense if the wearer is in the car. In response to detecting that the wearer is in the car within the prescribed period of time, a verbal alert or warning can be played back to the wearer by the hearing assistance device indicating that the wearer should not be driving.

After performing the Epley maneuver according to the techniques discussed herein, the wearer of the hearing assistance device can be reminded that they should keep their chin up and head straight throughout the day. The hearing assistance device can also remind the wearer not to lie flat in bed for the next 48 hours or on the side of the affected ear for 5 days. Timers for these events can be set by the hearing assistance device, and one or more sensors of the hearing assistance device (e.g., accelerometer, gyroscope, IMU) can be used to detect head/chin position and body orientation while in bed. Appropriate warnings can be played back to the wearer in response to the hearing assistance device detecting any of these events during the prescribed time periods.

Figure 8C:
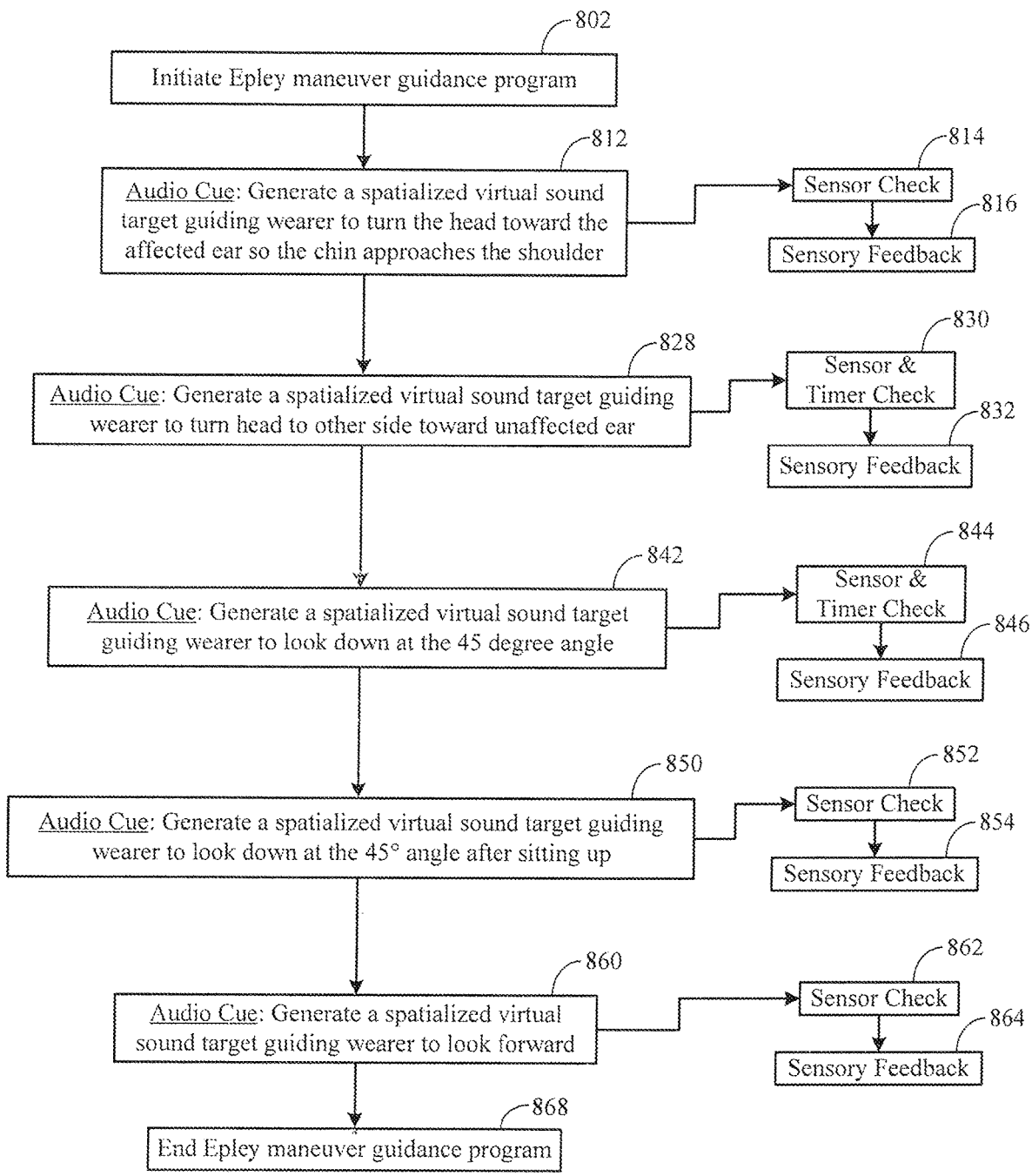
FIG. 8C is a flow chart showing various processes performed by a hearing assistance device that includes a virtual audio interface in accordance with various embodiments.

According to some embodiments, a hearing assistance device can be configured to execute an auditory guidance program that includes only spatialized virtual sound targets for implementing a predetermined corrective or therapeutic maneuver, physical therapy or exercise routine by a wearer of the hearing assistance device. For example, a wearer may not require verbal cues or prompts for a particular maneuver, therapy or routine, having executed same on numerous occasions. As such, the hearing assistance device need only generate a spatialized virtual sound target, perform a sensor check, and generate the appropriate sensory feedback for each action of a particular maneuver, therapy or routine. A wearer of a hearing assistance device, for example, may become very familiar with performing the Epley maneuver and prefer not to hear the verbal cues indicated in FIGS. 8A and 8B for efficiency. In this example, which is illustrated in FIG. 8C, the wearer can initiate an Epley maneuver guidance program 802 that involves the generation of spatialized virtual sound targets associated with audio cues 812, 828, 842, 850, and 860, with appropriate sensor check and sensory feedback operations 814, 816, 830, 832, 844, 846, 852, 854, 862, and 864 being performed for these audio cues. In the illustrative example shown in FIG. 8C, the virtual audio interface can provide auditory guidance through a therapeutic maneuver that uses sounds other than speech. It is understood that auditory guidance provided by the virtual audio interface using non-speech sounds can comprise spatialized 3-D virtual sounds, binaural sounds or monaural sounds, or a combination of these sounds.

It will be understood that a hearing assistance device that incorporates a virtual audio interface as described herein can be configured to guide a wearer through fitness exercises that involve body parts other than, or in addition to, the head and neck. For example, the previously described sensors, counters, and timers of the hearing assistance device can be used to track and count a variety of exercises, such as push-ups, sit-ups, pull-ups, and a variety of balance tests (e.g., the 30 second chair test and the timed up and go test (TUG)).

This document discloses numerous embodiments, including but not limited to the following:

Item 1 is a method implemented by a hearing assistance device adapted to be worn by a wearer, the method comprising:

generating, by the hearing assistance device, a sequence of audio cues that audibly guide the wearer through a series of actions involving the wearer's head and neck in accordance with a predetermined corrective or therapeutic maneuver;

sensing, using one or more sensors of the hearing assistance device, movement of the head during each of the actions;

determining, by a processor of the hearing assistance device, if head movement for an action associated with each audio cue has been correctly executed by the wearer; and producing, by the processor, an output indicative of successful or unsuccessful execution of the actions by the wearer.

Item 2 is the method of item 1, wherein the hearing assistance device comprises a single hearing assistance device adapted to be worn at or near an ear of the wearer.

Item 3 is the method of item 2, wherein the audio cues comprise speech specifying spatial locations where the wearer's head is to move.

Item 4 is the method of item 1, wherein the hearing assistance device comprises a pair of binaural hearing assistance devices adapted to be worn at or near the ears of the wearer.

Item 5 is the method of item 4, wherein the audio cues comprise stationary or moving spatialized virtual sound targets where the wearer's head is to follow, the spatialized virtual sound targets comprising one or more of speech, complex tones, noise bursts, and music.

Item 6 is the method of item 1, wherein producing the output comprises producing an audio output perceivable by the wearer, the audio output indicating successful or unsuccessful execution of each action or a series of actions taken by the wearer.

Item 7 is the method of item 1, wherein:

producing the output comprises producing an output signal communicated from the hearing assistance device to an external device; and the external device produces one or more of a visual, audible, and tactile output indicating successful or unsuccessful execution of each action or a series of actions by the wearer in response to the output signal.

Item 8 is the method of item 1, comprising:

receiving, by the hearing assistance device, the sequence of audio cues from an external source; and initiating the sequence of audio cues in response to an input received by the hearing assistance device.

Item 9 is the method of item 1, comprising:
  storing data associated with the predetermined corrective or therapeutic maneuver including the output by the hearing assistance device; and
  communicating the stored data from the hearing assistance device to an external device.

Item 10 is the method of item 1, wherein the predetermined corrective or therapeutic maneuver comprises actions for correcting Benign Paroxysmal Positional Vertigo or actions of a vestibular rehabilitation therapy.

Item 11 is a hearing assistance device adapted to be worn by a wearer, comprising:
  a processor configured to generate a sequence of audio cues that audibly guide the wearer through a series of actions involving the wearer's head and neck in accordance with a predetermined corrective or therapeutic maneuver;
  a speaker for playing back the sequence of audio cues for reception by the wearer; and
  one or more sensors configured to sense movement of the head during each of the actions;
  wherein the processor is configured to determine if head movement for an action associated with each audio cue has been correctly executed by the wearer, and produce an output indicative of successful or unsuccessful execution of the actions by the wearer.

Item 12 is the hearing assistance device of item 11, wherein the one or more sensors comprises one or more of an accelerometer, a gyroscope, and a magnetometer.

Item 13 is the hearing assistance device of item 11, wherein the one or more sensors comprises an eye movement sensor.

Item 14 is the hearing assistance device of item 11, wherein the hearing assistance device comprises a single hearing assistance device adapted to be worn at or near an ear of the wearer.

Item 15 is the hearing assistance device of item 14, wherein the audio cues comprise speech specifying spatial locations where the wearer's head is to move.

Item 16 is the hearing assistance device of item 11, wherein the hearing assistance device comprises a pair of binaural hearing assistance devices adapted to be worn at or near the ears of the wearer.

Item 17 is the hearing assistance device of item 16, wherein the audio cues comprise stationary or moving spatialized virtual sound targets where the wearer's head is to follow, the spatialized virtual sound targets comprising one or more of speech, complex tones, noise bursts, and music.

Item 18 is the hearing assistance device of item 11, wherein the processor is configured to produce an audio output for playback by the speaker, the audio output indicating successful or unsuccessful execution of each action or a series of actions by the wearer.

Item 19 is the hearing assistance device of item 11, wherein:
  the hearing assistance device comprises a transceiver coupled to the processor;
  the transceiver is configured to communicate the output from the processor to an external device; and
  the external device is configured to produce one or more of a visual, audible, and tactile output indicating successful or unsuccessful execution of each action or a series of actions by the wearer in response to the output received form the transceiver.

Item 20 is the hearing assistance device of item 11, wherein:
  the hearing assistance device comprises a memory and a transceiver respectively coupled to the processor;
  the memory is configured to store data associated with the predetermined corrective or therapeutic maneuver including the output from the processor; and
  the transceiver is configured to communicate the stored data to an external device.

Item 21 is the hearing assistance device of item 11, wherein the predetermined corrective or therapeutic maneuver comprises actions for correcting Benign Paroxysmal Positional Vertigo or actions of a vestibular rehabilitation therapy.

Although the subject matter has been described in language specific to structural features and/or methodological acts, it is to be understood that the subject matter defined in the appended claims is not necessarily limited to the specific features or acts described above. Rather, the specific features and acts described above are disclosed as representative forms of implementing the claims.

What is claimed is:

1. A method implemented by a hearing assistance device adapted to be worn by a wearer, the method comprising:
  generating, by the hearing assistance device, a first audio cue of a sequence of audio cues, wherein the first audio cue audibly instructs the wearer through a first action of a series of actions to perform themselves including their own head movement in accordance with a predetermined corrective or therapeutic maneuver, the predetermined corrective or therapeutic maneuver comprising actions for correcting Benign Paroxysmal Positional Vertigo or actions of a vestibular rehabilitation therapy;
  sensing, using one or more sensors of the hearing assistance device, movement of the wearer's head during the first action;
  determining, by a processor of the hearing assistance device, whether head movement for the first action associated with the first audio cue has been successfully executed by the wearer;
  after determining whether the head movement for the first action has been successfully executed by the wearer:
    producing, by the processor, an audio output as explicit feedback for the wearer indicative of successful or unsuccessful execution of the first action by the wearer; and
    modifying, by the hearing assistance device, a second audio cue of the sequence of audio cues depending on the successful or unsuccessful execution of the first action by the wearer; and
    generating, by the hearing assistance device, the second audio cue of the sequence of audio cues wherein the second audio cue audibly instructs the wearer through a second action of the series of actions.

2. The method of claim 1, wherein the hearing assistance device comprises a single hearing assistance device adapted to be worn at or near an ear of the wearer.

3. The method of claim 2, wherein the audio cues comprise speech specifying spatial locations where the wearer's head is to move.

4. The method of claim 1, wherein the hearing assistance device comprises a pair of binaural hearing assistance devices adapted to be worn at or near the ears of the wearer.

5. The method of claim 4, wherein the audio cues comprise stationary or moving spatialized virtual sound targets where the wearer's head is to follow, the spatialized virtual sound targets comprising one or more of speech, complex tones, noise bursts, and music.

6. The method of claim 1, the audio output indicating successful or unsuccessful execution of each action or a series of actions taken by the wearer.

7. The method of claim 1, wherein:
producing the output comprises producing an output signal communicated from the hearing assistance device to an external device; and
the external device produces one or more of a visual, audible, and tactile output indicating successful or unsuccessful execution of each action or a series of actions by the wearer in response to the output signal.

8. The method of claim 1, comprising:
receiving, by the hearing assistance device, the sequence of audio cues from an external source; and
initiating the sequence of audio cues in response to an input received by the hearing assistance device.

9. The method of claim 1, comprising:
storing data associated with the predetermined corrective or therapeutic maneuver including the output by the hearing assistance device; and
communicating the stored data from the hearing assistance device to an external device.

10. The method of claim 1, wherein the predetermined corrective or therapeutic maneuver is the Epley maneuver.

11. The method of claim 1, further comprising:
issuing a verbal warning upon determining that the wearer is in the car during the prescribed period of time.

12. The method of claim 1, further comprising instructing the wearer to lie down prior to the first audio cue of the sequence of audio cues.

13. A hearing assistance device adapted to be worn by a wearer, comprising:
a processor configured to generate a sequence of audio cues that audibly instruct the wearer through a series of actions involving movement of the wearer's own head and neck in accordance with a predetermined corrective or therapeutic maneuver, the predetermined corrective or therapeutic maneuver comprising actions for correcting Benign Paroxysmal Positional Vertigo or actions of a vestibular rehabilitation therapy;
a speaker for playing back the sequence of audio cues for reception by the wearer; and
one or more sensors configured to sense movement of the wearer's head during each of the actions;
wherein the processor is configured to determine whether head movement for an action associated with each audio cue has been successfully executed by the wearer, produce an audio output for playback by the speaker as explicit feedback for the wearer indicative of successful or unsuccessful execution of each action by the wearer, and modify the sequence of audio cues depending on the successful or unsuccessful execution of each action by the wearer.

14. The hearing assistance device of claim 13, wherein the one or more sensors comprises one or more of an accelerometer, a gyroscope, and a magnetometer.

15. The hearing assistance device of claim 13, wherein the one or more sensors comprises an eye movement sensor.

16. The hearing assistance device of claim 13, wherein the audio cues comprise speech specifying spatial locations where the wearer's head is to move.

17. The hearing assistance device of claim 13, wherein the hearing assistance device comprises a pair of binaural hearing assistance devices adapted to be worn at or near the ears of the wearer.

18. The hearing assistance device of claim 17, wherein the audio cues comprise stationary or moving spatialized virtual sound targets where the wearer's head is to follow, the spatialized virtual sound targets comprising one or more of speech, complex tones, noise bursts, and music.

19. The hearing assistance device of claim 13, wherein:
the hearing assistance device comprises a transceiver coupled to the processor;
the transceiver is configured to communicate the output from the processor to an external device; and
the external device is configured to produce one or more of a visual, audible, and tactile output indicating successful or unsuccessful execution of each action or a series of actions by the wearer in response to the output received form the transceiver.

20. The hearing assistance device of claim 13, wherein:
the hearing assistance device comprises a memory and a transceiver respectively coupled to the processor;
the memory is configured to store data associated with the predetermined corrective or therapeutic maneuver including the output from the processor; and
the transceiver is configured to communicate the stored data to an external device.

21. A method implemented by a hearing assistance device adapted to be worn by a wearer, the method comprising:
generating, by the hearing assistance device, a sequence of audio cues that audibly instruct the wearer through a first action of a series of actions to perform themselves including their own head movement in accordance with a predetermined corrective or therapeutic maneuver;
sensing, using one or more sensors of the hearing assistance device, movement of the wearer's head during each of the actions;
determining, by a processor of the hearing assistance device, whether head movement for an action associated with each audio cue has been successfully executed by the wearer;
producing, by the processor, an audio output as explicit feedback for the wearer indicative of successful or unsuccessful execution of the action by the wearer; and
generating, by the hearing assistance device, a sequence of audio cues that audibly instruct the wearer through a subsequent action of the series of actions based on the successful or unsuccessful execution of the first action.

* * * * *